United States Patent [19]

Da Col et al.

[11] Patent Number: 5,589,593

[45] Date of Patent: Dec. 31, 1996

[54] CRYSTALLINE FORM OF A CEPHALOSPORIN ANTIBIOTIC

[75] Inventors: Marco Da Col, Bologna; Leone Dall'Asta, Pavia; Irene Resta, Milan, all of Italy

[73] Assignee: Biochimica Opos SpA, Agrate Brianza, Italy

[21] Appl. No.: 483,888

[22] Filed: Jun. 7, 1995

Related U.S. Application Data

[62] Division of Ser. No. 455,136, May 31, 1995, which is a continuation of Ser. No. 235,262, Apr. 29, 1994, abandoned, which is a continuation of Ser. No. 973,457, Nov. 9, 1992, abandoned.

[30] Foreign Application Priority Data

Nov. 11, 1991 [IT] Italy ................................ MI91A2995

[51] Int. Cl.$^6$ .................................................. C07D 501/32
[52] U.S. Cl. ............................................. 540/220; 540/215
[58] Field of Search ...................................... 540/220, 215

[56] References Cited

U.S. PATENT DOCUMENTS

| | | | |
|---|---|---|---|
| 3,925,372 | 12/1975 | Chauvette | 260/243 C |
| 4,898,938 | 2/1990 | Manuli | 540/230 |
| 5,142,042 | 8/1992 | Chang et al. | 540/215 |
| 5,409,918 | 4/1995 | Adam et al. | 540/222 |

FOREIGN PATENT DOCUMENTS

0429895A1  6/1991  European Pat. Off. .

OTHER PUBLICATIONS

Journal of Medicinal Chemistry vol. 18, No. 14, Apr. 1975 Washington pp. 403–408.

Lorenz, Analytical Profile of Drug Substances, pp. 108–123 (1980) Academic Press.

*Primary Examiner*—John M. Ford
*Assistant Examiner*—Pavanaram K. Sripada
*Attorney, Agent, or Firm*—Nikaido, Marmelstein, Murray & Oram LLP

[57] ABSTRACT

The preparation of a novel crystalline cefaclor and the conversion of such a product to cefaclor monohydrate are described. The new intermediate cefaclor is a particular crystalline form and possesses the same antibiotic properties as cefaclor monohydrate.

3 Claims, 2 Drawing Sheets

CRYSTALLINE FORM OF A CEPHALOSPORIN ANTIBIOTIC

This is a division of application Ser. No. 08/455,136, filed May 31, 1995, which is a continuation of application Ser. No. 08/235,262 filed Apr. 29, 1994, now abandoned which is a continuation of application Ser. No. 07/973,457 filed Nov. 9, 1992, now abandoned.

The present invention concerns a novel crystalline form of cefaclor, a process for its preparation and for its conversion to cefaclor monohydrate, as well as pharmaceutical compositions containing it as active ingredient.

"Cefaclor" is the International Non-proprietary Name for 7β-(D-2-amino-2-phenylacetamido)-3-chloro-3-cephem-4-carboxylic acid, represented by the formula (A),

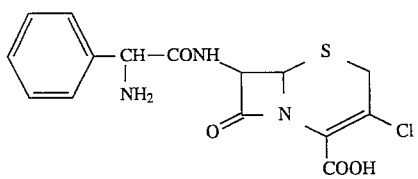

which is an orally active cefalosporin antibiotic.

Cefaclor for pharmaceutical use is a monohydrate, namely a compound of formula (A) with a molecule of water of crystallization.

The preparation of cefaclor monohydrate, which is not described in the literature, involves a lot of difficulties due to the crystalline form itself of the antibiotic and to the methods for the synthesis of such an active principle, which involve the use of polar aprotic solvents.

U.S. Pat. No. 3,925,372 discloses the preparation of cefaclor by reaction of the methyl sodium Dane salt of D-phenylglycine with 7-amino-3-chloro-3-cephem-4-carboxylic acid as silyl derivative and the isolation of cefaclor as hemihydrate.

The preparation of cefaclor is also described by R. R. Chauvette and P. A. Pennington in J. Med. Chem. 1975, 18, 403–408. By reacting the methyl sodium Dane salt of D-phenylglycine with p-nitrobenzyl 7-amino-3-chloro-3-cephem-4-carboxylate and by hydrogenating the product thus obtained in the presence of palladium on charcoal, cefaclor is obtained which crystallizes as hemihydrate.

It has now been found that, starting from a raw cefaclor, a novel crystalline form of cefaclor is obtained, containing a water percent lower than that of the monohydrate and higher than that of the hemihydrate.

It has also surprisingly found that this new crystalline form of cefaclor is stable in whatever moisture conditions and allows its use in pharmaceutical formulations which have the advantage, in respect of those comprising the monohydrate, of containing a higher amount of active ingredient per weight unit. By contrast, the hemihydrate form is difficult to obtain in a reproducible way because of its instability. Finally, it has been found that the novel crystalline cefaclor, which cannot be reconstituted by simple treatment with water in the warm, can be converted to cefaclor monohydrate.

For this purpose, it must be dissolved in acidic medium and precipitated in crystalline form at a suitable pH to isolate said monohydrate.

Thus, it is an object of the present invention to provide a novel crystalline form of cefaclor containing from 2.5% to 4.3% of water, advantageously from 2.6% to 4.2%. Preferably, the crystalline cefaclor of the invention contains 3.5% of water.

The crystalline cefaclor of the present invention exhibits the X-rays diffraction pattern set forth in Table I. Such pattern, different from that of cefaclor monohydrate, has been detected, with the product of the present invention, as a powder, by using a PW diffractometer in the usual diffraction conditions (copper Kα radiations; curve graphite crystal monochromator). The interplanar spacings are denoted as "d(A)" and the relative intensities are in the column "I %".

TABLE I

| d(A) | I % |
|------|-----|
| 11,55 | 67 |
| 9,56 | 8 |
| 8,45 | 17 |
| 7,93 | 29 |
| 6,72 | 8 |
| 5,94 | 15 |
| 5,78 | 22 |
| 5,59 | 28 |
| 5,38 | 11 |
| 5,19 | 97 |
| 4,83 | 56 |
| 4,62 | 3 |
| 4,51 | 8 |
| 4,44 | 11 |
| 4,27 | 100 |
| 4,06 | 15 |
| 3,97 | 83 |
| 3,87 | 9 |
| 3,79 | 7 |
| 3,68 | 2 |
| 3,59 | 28 |
| 3,53 | 13 |
| 3,47 | 38 |
| 3,34 | 15 |
| 3,25 | 18 |
| 3,18 | 31 |
| 3,08 | 33 |
| 2,94 | 12 |
| 2,89 | 7 |
| 2,81 | 10 |
| 2,74 | 7 |

It is another object of the present invention to provide a process for the preparation of the new crystalline cefaclor, characterized in that cefaclor is treated with a mineral or organic acid in a from about 4/1 (v/v) to about 1/4 (v/v) mixture of water and a substantially water-miscible alcohol until a complete solution is obtained, then the pH of the solution is adjusted to about 4.5, the temperature is brought to 0°–5° C. and the product thus obtained is isolated.

The cefaclor used as starting material may be a raw cefaclor obtained according to one of the methods described in the literature, for example according to U.S. Pat. No. 3,925,372 or to J. Med. Chem. 1975, 18, 403–408 (to which reference is made herein for further details), by excluding the final operation of recovery of the product as hemihydrate.

A raw cefaclor particularly suitable as starting material is an amorphous cefaclor obtained by reacting a D-phenylglycine Dane salt, preferably the ethyl 3-α-carboxybenzylaminocrotonate potassium salt (obtained from D-phenylglycine and ethyl acetoacetate), with the triethylamine salt of 7-amino-3-chloro-3-cephem-4-carboxylic acid in an acetonitrile/dimethylformamide/water mixture and isolating the product by acidification of the mixture and correction of pH to a value of 4.5. Crystalline cefaclor with different hydration degree as well as cefaclor in a solar form may also be used as starting materials.

The alcohol-water mixture used for the preparation of crystalline cefaclor consists in preferably deionized water and in a water-miscible alcohol, preferably an aliphatic alcohol containing from 1 to 4 carbon atoms, from example methanol, ethanol, isopropanol.

The amount of the mineral or organic acid used is that which allows the solution of the raw cefaclor. Suitable acids, for example, are hydrochloric, hydrobromic, sulfuric, phosphoric, methanesulfonic, trifluoroacetic acids. Preferably an aqueous solution of hydrochloric acid is used.

Crystalline cefaclor is isolated at a pH of about 4.5 by simple cooling and filtration.

The pH of about 4.5 is reached by treating the acid solution with an inorganic or organic base such as an alkaline hydroxide, for example sodium hydroxide, ammonium hydroxide, or an amine, for example trimethylamine, triethylamine, N-metilpiperidine, N-methylmorpholine, triethylamine and ammonium hydroxide being the preferred bases.

The product thus obtained is stable and may be used as such for the preparation of oral pharmaceutical compositions, for example in gelatine capsules, tablets, granulates, alone or in admixture with the usual pharmaceutical carriers. Such pharmaceutical compositions comprise crystalline cefaclor according to the present invention in amounts equivalent to 125–750 mg, preferably 250 or 500 mg, of anhydrous cefaclor.

Alternatively, crystalline cefaclor thus obtained may be used for the preparation of cefaclor monohydrate. Such an use is provided by a further object of the present invention. Such an use involves a process for the conversion of crystalline cefaclor into cefaclor monohydrate which comprises acidifying an aqueous suspension of the above described crystalline cefaclor until a complete solution is obtained, adjusting the pH to about 4.5 and isolating the product thus obtained.

Preferably the process is carried out by acidifying an aqueous suspension of crystalline cefaclor until a complete solution is obtained, then by increasing the pH of the solution to 1.5.

The monohydrate begins to precipitate or a crystal of authentic cefaclor monohydrate is added to initiate the precipitation. By adjusting the pH of the solution to about 4.5 at room temperature (20°÷30° C.) slowly and cooling, the precipitation is completed and cefaclor monohydrate is recovered by filtration.

Preferably, crystalline cefaclor is dissolved by using a mineral or organic acid such as hydrochloric, hydrobromic, sulphuric, phosphoric, methanesulfonic or trifluoroacetic acid and the increase of pH to about 4.5 is obtained by using a inorganic or organic base like those above mentioned, for example ammonium hydroxide, sodium hydroxide, trimethyl amine or triethylamine, triethylamine and ammonium hydroxide being preferred.

Thus cefaclor, preferably in amorphous form, may be converted to cefaclor monohydrate by a two-steps process, which comprises (i) treating cefaclor with a mineral or organic acid in a from about 4/1 (v/v) to about 1/4 (v/v) mixture of water and a substantially water-miscible alcohol until a complete solution is obtained, adjusting the pH of the solution to about 4.5, bringing the temperature of the solution to 0°÷5° C. and isolating the crystalline cefaclor thus obtained; then (ii) acidifying an aqueous suspension of said crystalline cefaclor until a complete solution is obtained, adjusting the pH to about 4.5 and isolating the cefaclor monohydrate thus obtained.

BRIEF DESCRIPTION OF THE DRAWING FIGURES

Figure 1:
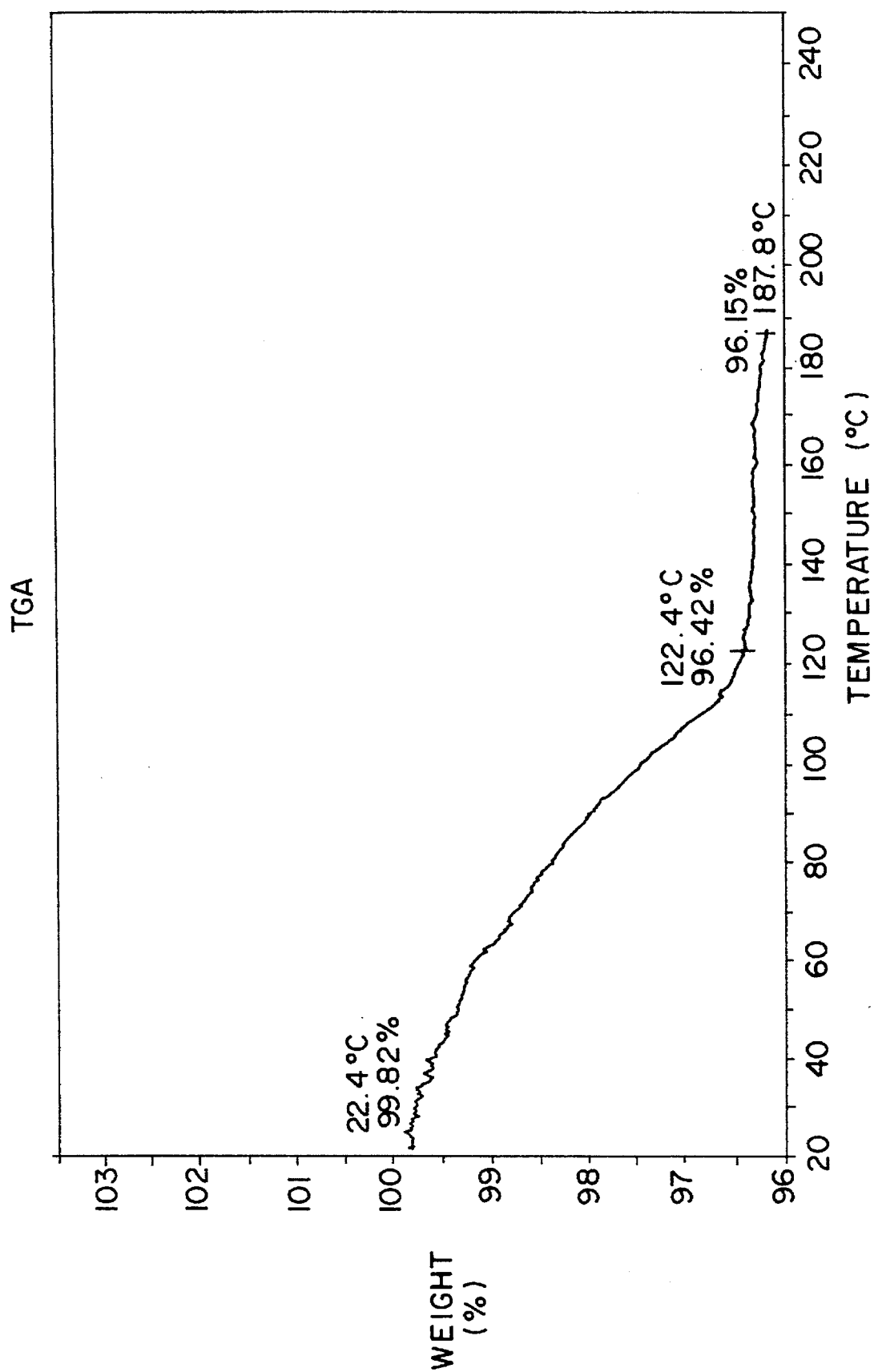
FIG. 1 is a plot of a thermogravimetric analysis of the product formed in Example 3.

The following examples illustrate the invention without, however, limiting it.

EXAMPLE 1

Amorphous raw cefaclor

To a mixture of 162 g of ethyl 3-α-carboxybenzylaminocrotonate potassium salt, 450 ml of dimethylformamide and 900 ml of acetonitrile, cooled to −40° C., 1.5 ml of 4-methylmorpholine and 54 ml of ethyl chloroformate are added. The mixture is stirred one hour at −40° C., then a previously cooled solution of triethylamine salt of 7-amino-3-chloro-3-cephem-4-carboxylic acid (corresponding to 99 g of free acid) in 900 ml of a mixture acetonitrile/water 1/1 (v/v) is added thereinto. The solution is kept in the cool for about 3 hours, then it is treated with 630 ml of water and filtered. The filtrate is made acid to pH 1.5 with 6N hydrochloric acid, then the pH is adjusted to 4.5 with triethyl amine. The suspension thus obtained is kept to 0° C. overnight, then it is filtered. The product thus obtained is washed with acetonitrile/water 1/1 (v/v) and dried under vacuum at 35° C. Thus, 120 g of amorphous raw cefaclor are obtained.

EXAMPLE 2

(a) Condensation

To a mixture of 300 ml of acetonitrile and 180 ml of dimethyl formamide, at 0° C., 54 g of ethyl 3-α-carboxybenzylaminocrotonate potassium salt are added. The mixture is cooled to −40° C. and 18 ml of ethyl chloroformate and 0.25 ml of 4-methylmorpholine are added thereinto. The mixture is kept one hour at −40° C., then it is treated with a previously to 0° C. cooled solution of silylated 7-amino-3-chloro-3-cephem-4-carboxylic acid (obtained from 33 g of free acid with bis-trimethylsilylacetamide) in 300 ml of aceto nitrile. The solution is kept 2 hours at −40° C., then it is diluted with 210 ml of water, acidified with 6N hydrochloric acid to pH 1.5 and filtered to eliminate the undissolved products. The pH of the clear solution is adjusted to 4.5 with triethylamine and the suspension is filtered.

(b) Crystallization

The wet product thus obtained is dissolved in a with diluted hydrochloric acid acidified mixture of 250 ml of water and 250 ml of methanol. The mixture is decolorized with charcoal, filtered, cooled to +5° C. and brought to pH 4.5 with triethylamine.

Then it is filtered, the product is washed with water and dried "in vacuo" at 35° C.

Thus, 30.4 g of crystalline cefaclor containing 2.8% of water are obtained.

EXAMPLE 3

(a) Condensation

To a previously to −40° C. cooled mixture of 300 ml of acetonitrile, 180 ml of dimethylformamide and 54 g of ethyl 3-α-carboxybenzyl aminocrotonate potassium salt, 18 ml of ethyl chloroformate and 0.25 ml of 4-methylmorpholine are added. After one hour at −40° C. a solution at 0° C. of the 7-amino-3-chloro-3-cephem-4-carboxylic acid triethylamine salt (obtained from 33 g of free acid and triethyl amine) in 300 ml of acetonitrile/water 1/1 (v/v) is added thereinto. The solution is kept 3 hours at −40° C. under stirring, then water is added thereinto and the undissolved part is eliminated by filtration. The clear solution is made acid with 6N hydrochloric acid until pH 1.5, then the pH is adjusted to 4.5 with triethyl amine and the product obtained is filtered and washed with acetonitrile/water 2/1 (v/v).

(b) Crystallization

To a suspension of the wet product thus obtained in 500 ml of a mixture methanol/water 1/1 (v/v), 6N hydrochloric acid is added until a clear solution is obtained. The solution is decolorized with charcoal and filtered. Its pH is adjusted to a final value of 4.5 by slow addition of triethylamine. The solution is cooled to 0° C. and kept at this temperature for 2 hours, then it is filtered, washed with cool water and dried at 40° C. "in vacuo".

Thus, 32 g of crystalline cefaclor containing 3.5% of water and having a HPLC purity of 98% are obtained.

The thermogravimetric analysis (TGA) of the product shows, from 22° to 120° C., a weight loss of about 3.5% which exactly corresponds to the crystallization water, as appears in FIG. 1.

Figure 2:
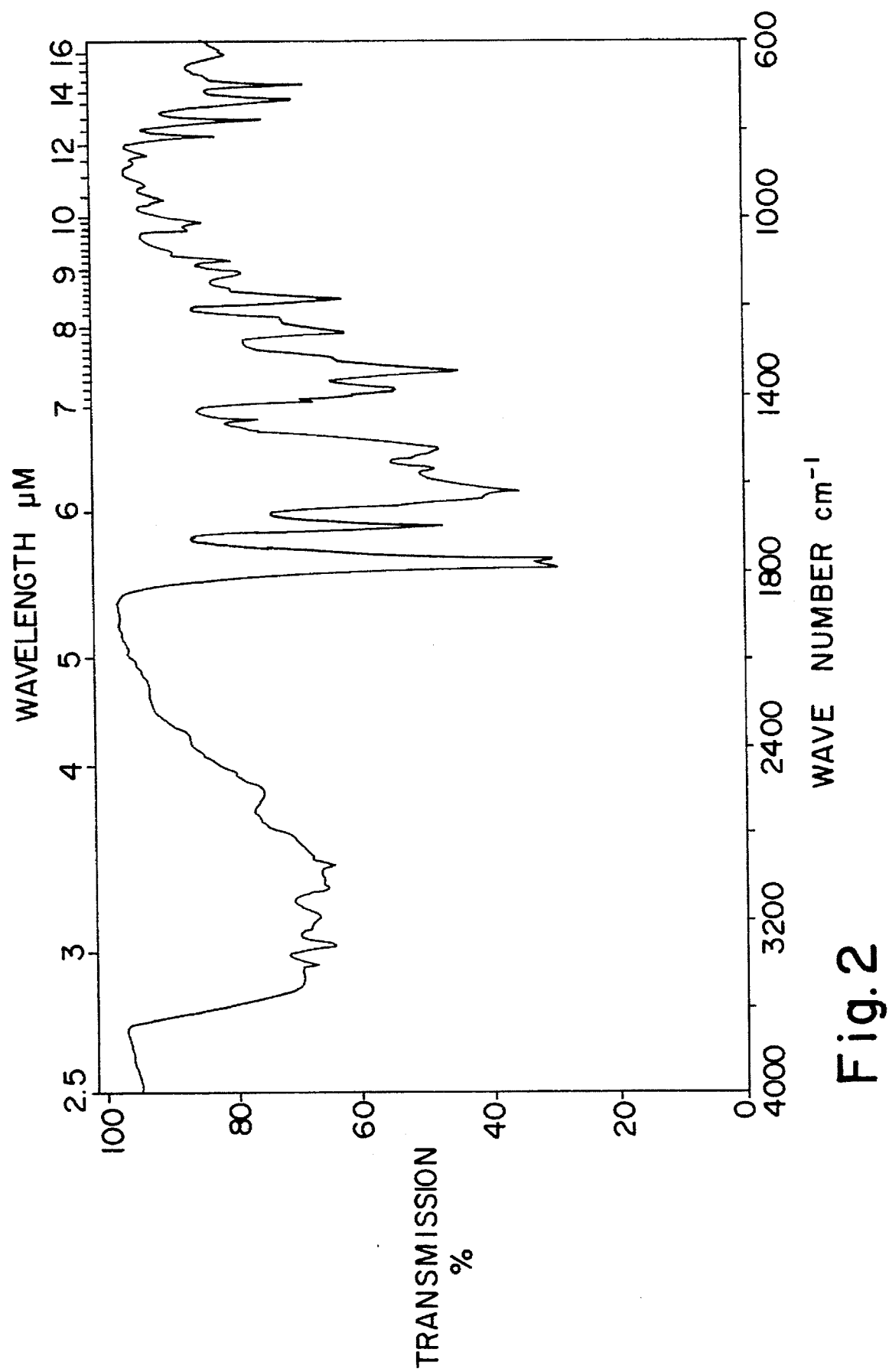
FIG. 2 is a plot of IR spectrum of the product of Example 3.

FIG. 2 shows the IR spectrum of the product in KBr.

EXAMPLE 4

Crystallization

To a suspension of 11 g of amorphous raw cefaclor, obtained as described in Example 1, in 66 ml of a mixture methanol/water 2/1 (v/v), 6N hydrochloric acid is added until a clear solution is obtained.

This solution is decolorized with charcoal, its pH is adjusted with triethylamine to reach a value of 4.5 in 2 hours, then it is cooled to 0° C., kept at this temperature for 2 hours and finally filtered. The recovered product is washed with a mixture methanol/water 2/1 (v/v) and dried under vacuum.

Thus, 8.2 g of crystalline cefaclor containing 2.8% of water are obtained.

EXAMPLE 5

Crystallization

To a suspension of 20 g of raw cefaclor, obtained as described in Example 1, in 90 ml of a solution methanol/water 2/1 (v/v), 6N hydrochloric acid is added until a complete solution is obtained. This solution is decolorized, filtered and treated, in about 90 minutes at 0° C., with 50 ml of water, by keeping the pH constant at 4.5 by concurrent addition of triethylamine. The suspension is kept one hour at 0° C., then it is filtered and the recovered product is dried under vacuum.

Thus, 14.8 g of crystalline cefaclor containing 3.2% of water are obtained.

EXAMPLE 6

Crystallization

To a suspension of 36 g of amorphous raw cefaclor, obtained as described in Example 1, in 300 ml of a solution ethanol/water 1/1 (v/v), 6N hydrochloric acid is added until a complete solution is obtained. This solution is decolorized with charcoal, filtered and its pH is adjusted by addition of triethylamine to reach the value of 4.5 in about 2 hours. Then it is cooled to 0°/+5° C., kept at this temperature for additional 2 hours and filtered. The product recovered is washed with water and dried under vacuum.

Thus, 28.5 g of crystalline cefaclor containing 3.7% of water are obtained.

EXAMPLE 7

Crystallization

To a suspension of 10 g of amorphous raw cefaclor, obtained as described in Example 1, in 60 ml of isopropanol/water 1/4 (v/v) 6N hydrochloric acid is added until the obtention of a solution which is decolorized with charcoal and filtered. The pH of the solution is adjusted to reach the value of 4.5 in 180 minutes by addition of triethylamine. The solution is cooled to 0° C., kept at this temperature overnight, then filtered. The recovered product is washed with water and dried under vacuum at 40° C.

Thus, 7.8 g of crystalline cefaclor containing 4.1% of water are obtained.

EXAMPLE 8

Crystallization

To a mixture of 550 ml of methanol and 550 ml of deionized water 114 g of amorphous raw cefaclor, obtained as described in Example 1, are suspended. To the suspension 70 ml of 6N hydrochloric acid are added in 30 minutes under stirring, whereby a complete solution is obtained (pH of about 1.5). After decolorizing with charcoal, triethylamine is slowly added to the clear solution to a pH value of 2.1. The solution is stirred until crystallization begins, then triethylamine is added again until a pH of 4.5 is obtained and the crystallization is thus complete. The mixture is cooled to 0° C. and kept 2 hours at this temperature, then it is filtered. The recovered product is washed with deionized cool water and dried under vacuum.

Thus, 84 g of crystalline cefaclor containing 3.5% water are obtained. In the following examples some illustrative pharmaceutical formulations for oral use containing crystalline cefaclor are given.

EXAMPLE 9

Tablets containing:

| | |
|---|---|
| crystalline cefaclor (containing 3,5% water) equivalent to 250 mg of anhydrous cefaclor | 259 mg |
| sodium laurylsulfate | 5 mg |
| starch | 10 mg |
| microcrystalline cellulose q.s. to | 500 mg |

EXAMPLE 10

Hard Gelatine Capsules containing:

| | |
|---|---|
| crystalline cefaclor (containing 3,5% water) equivalent to 500 mg of anhydrous cefaclor | 518 mg |
| starch | 6–12 mg |
| finely subdivided silica | 3–6 mg |

EXAMPLE 11

Granulate for reconstituted suspension (250 mg/5 ml) containing:

| | |
|---|---|
| crystalline cefaclor (containing 3,5% water) equivalent to 250 mg of anhydrous cefaclor | 259 mg |
| low viscosity sodium carboxymethylcellulose | 90 mg |
| orange flavour | 5 mg |
| starch | 15 mg |
| sucrose | 1800 mg |

EXAMPLE 12

Preparation of cefaclor monohydrate

To a suspension of 82 g of crystalline cefaclor, obtained as described in Example 7, in 500 ml of deionized water 50 ml of 6N hydrochloric acid are added under stirring at about 15° C. until a complete solution is obtained. The solution thus obtained, having a pH of about 0.7, is decolorized, then ammonium hydroxide is added to the clear solution at pH 1.5. The crystallization is initiated by crystalline cefaclor monohydrate as seed, then ammonium hydroxide is added again in 4 hours up to a constant pH of 4.5. The mixture is kept under stirring for 30 minutes at 25° C., then it is cooled at about 0° C. and kept 2 hours at 0°÷5° C. The recovered product is filtered, washed with cool deionized water and dried under vacuum at 35° C.

Thus, 67–68 g of crystalline cefaclor monohydrate are obtained. It's IR and X-rays analysis is in agreement with the official standard.

We claim:

1. A process for the preparation of crystalline cefaclor and for its conversion to cefaclor monohydrate, which comprises (i) treating raw cefaclor with a mineral or organic acid in a from about 4/1 (v/v) to about 1/4 (v/v) mixture of water and a substantially water-miscible alcohol until a complete solution is obtained, adjusting the pH of the solution to about 4.5, bringing the temperature of the solution to 0°–5° C. and isolating the crystalline cefaclor thus obtained; then (ii) acidifying an aqueous suspension of said crystalline cefaclor until a complete solution is obtained, adjusting the pH to about 4.5 and isolating the cefaclor monohydrate thus obtained.

2. A process as recited in claim 1, wherein said raw cefaclor is amorphous cefaclor.

3. A process as recited in claim 1, wherein said raw cefaclor is a crystalline cefaclor having a hydratation degree different from 2.5 to 4.3%.

* * * * *